(12) United States Patent
Huang et al.

(10) Patent No.: US 9,180,260 B2
(45) Date of Patent: Nov. 10, 2015

(54) SYSTEMS AND METHODS FOR MONITORING AN INJECTION PROCEDURE

(71) Applicant: Covidien LP, Mansfield, MA (US)

(72) Inventors: Qiaojian Huang, Broomfield, CO (US); Youzhi Li, Longmont, CO (US); Sarah Hayman, Boulder, CO (US); Keith Manning, Linlithgow (GB)

(73) Assignee: Covidien LP, Mansfield, MA (US)

( * ) Notice: Subject to any disclaimer, the term of this patent is extended or adjusted under 35 U.S.C. 154(b) by 6 days.

(21) Appl. No.: 14/015,676

(22) Filed: Aug. 30, 2013

(65) Prior Publication Data

US 2015/0065956 A1 Mar. 5, 2015

(51) Int. Cl.
*A61M 5/50* (2006.01)
*F16K 31/122* (2006.01)
*F16K 15/06* (2006.01)
*F16K 37/00* (2006.01)
*A61M 39/24* (2006.01)

(52) U.S. Cl.
CPC ............ *A61M 5/5086* (2013.01); *F16K 15/063* (2013.01); *F16K 31/1221* (2013.01); *F16K 37/0075* (2013.01); *A61M 2039/242* (2013.01); *A61M 2205/14* (2013.01)

(58) Field of Classification Search
CPC ... F16K 31/122; F16K 37/0075; F16K 31/12; F16K 37/00; F16K 37/0083; F16K 27/0209; F16K 15/026; F16K 15/06; F16K 15/00; F16K 15/025; F16K 15/063; F16K 15/02; F16K 15/021; A61M 39/26; A61M 2039/242; A61M 39/24; A61M 2039/2473; A61M 2039/2486
See application file for complete search history.

(56) References Cited

U.S. PATENT DOCUMENTS

| 4,004,576 | A | | 1/1977 | Gahwiler et al. |
| 4,407,298 | A | | 10/1983 | Lentz et al. |
| 4,841,981 | A | | 6/1989 | Tanabe et al. |
| 4,887,469 | A | * | 12/1989 | Shoptaw ..................... 73/861.77 |
| 4,915,591 | A | * | 4/1990 | Funke ............................ 417/18 |

(Continued)

FOREIGN PATENT DOCUMENTS

| EP | 1579800 | 9/2005 |
| EP | 1632264 | 8/2006 |

(Continued)

OTHER PUBLICATIONS

Xu, M., et al.; "Photoacoustic imaging in biomedicine," Rev. Sci. Instrum. 77, 041101 (2006).

(Continued)

*Primary Examiner* — Kevin C Sirmons
*Assistant Examiner* — William Carpenter
(74) *Attorney, Agent, or Firm* — Fletcher Yoder PC

(57) ABSTRACT

An indicator dilution system includes a catheter configured to deliver an indicator to a patient, an injection device configured to deliver the indicator to the catheter, and a connector coupling the injection device to the catheter. The system also includes one or more sensors configured to acquire measurements from components of the system, which may be used to determine the start and end time of the injection of the indicator to the patient. For example, the one or more sensors may be configured to acquire signals relating to a state of the connector, which may be used to determine whether the connector is in an open state to enable flow of the indicator or in a closed state to reduce flow of the indicator.

35 Claims, 8 Drawing Sheets

(56) References Cited

U.S. PATENT DOCUMENTS

| | | | |
|---|---|---|---|
| 5,232,582 A * | 8/1993 | Takahashi et al. | 210/86 |
| 5,979,497 A * | 11/1999 | Cullerton | 137/533.29 |
| 6,200,301 B1 | 3/2001 | Pfeiffer et al. | |
| 6,231,498 B1 | 5/2001 | Pfeiffer et al. | |
| 6,299,132 B1 * | 10/2001 | Weinheimer et al. | 251/149.6 |
| 6,623,436 B2 | 9/2003 | Krivitski et al. | |
| 6,939,307 B1 | 9/2005 | Dunlop | |
| 7,024,235 B2 * | 4/2006 | Melker et al. | 600/340 |
| 7,132,641 B2 | 11/2006 | Schulz et al. | |
| 7,201,734 B2 | 4/2007 | Hickle | |
| 7,280,858 B2 | 10/2007 | Al-Ali et al. | |
| 7,367,954 B2 | 5/2008 | Starr et al. | |
| 7,376,452 B2 | 5/2008 | Kobayashi et al. | |
| 7,869,850 B2 * | 1/2011 | Hoarau et al. | 600/344 |
| 8,308,440 B2 * | 11/2012 | Shirai | 417/28 |
| 2002/0004015 A1 * | 1/2002 | Carlisle et al. | 417/479 |
| 2006/0173258 A1 | 8/2006 | Kobayashi et al. | |
| 2006/0224053 A1 | 10/2006 | Black et al. | |
| 2006/0253007 A1 | 11/2006 | Cheng et al. | |
| 2007/0062531 A1 | 3/2007 | Fisher et al. | |
| 2007/0084766 A1 * | 4/2007 | Ishii et al. | 210/87 |
| 2007/0088216 A1 | 4/2007 | Pfeiffer et al. | |
| 2007/0093702 A1 | 4/2007 | Yu et al. | |
| 2007/0093752 A1 * | 4/2007 | Zhao et al. | 604/131 |
| 2007/0118045 A1 | 5/2007 | Naghavi et al. | |
| 2007/0197859 A1 | 8/2007 | Schaer et al. | |
| 2008/0015451 A1 | 1/2008 | Hatib et al. | |
| 2008/0081969 A1 | 4/2008 | Feldman et al. | |
| 2008/0255433 A1 | 10/2008 | Prough et al. | |
| 2008/0262418 A1 | 10/2008 | Burnett et al. | |
| 2010/0305446 A1 | 12/2010 | Berard-Anderson et al. | |
| 2011/0009821 A1 | 1/2011 | Jespersen et al. | |
| 2011/0048556 A1 * | 3/2011 | Carter et al. | 137/559 |
| 2011/0313349 A1 | 12/2011 | Krulevitch et al. | |
| 2012/0199218 A1 * | 8/2012 | Gioberti et al. | 137/511 |
| 2013/0119150 A1 * | 5/2013 | Cesak et al. | 239/74 |
| 2013/0137959 A1 | 5/2013 | Lisogurski et al. | |
| 2013/0137960 A1 | 5/2013 | Lisogurski et al. | |
| 2014/0039595 A1 * | 2/2014 | Kroll-Orywahl et al. | 607/149 |
| 2014/0046303 A1 * | 2/2014 | Donaldson | 604/540 |
| 2014/0066860 A1 * | 3/2014 | Houfburg et al. | 604/207 |
| 2014/0066891 A1 * | 3/2014 | Burns et al. | 604/506 |

FOREIGN PATENT DOCUMENTS

| | | |
|---|---|---|
| EP | 1847218 | 10/2007 |
| JP | 2012026484 A * | 2/2012 |
| WO | WO9953834 | 10/1999 |
| WO | WO 0204895 A2 * | 1/2002 |
| WO | WO2007051066 | 5/2007 |
| WO | WO 2012126124 A1 * | 9/2012 |

OTHER PUBLICATIONS

Reuter, D.A. et al.; "Cardiac Output Monitoring Using Indicator-Dilution Techniques: Basics, Limits, and Perspectives," Anesthesia 110, 799 (2010).

PiCCO2 Setup Guide; Pulsion Medical Systems; http://www.pulsion.com/fileadmin/pulsion_share/Products_Flyer/PiCCO_US_ALL/PiCCO2_A4_Setup_MPI851505US_R00_271109_low.pdf; Jan. 2010.

Product Catalog; Pulsion Medical Systems; http://www.pulsion.com/fileadmin/pulsion_share/Products_Flyer/Productcatalogue_E_MPI700205_R03_040708.pdf; Jul. 2008.

Deltran Technology for Critical Care; Utah Medical Products, Inc.; http://www.utahmed.com/pdf/5831.pdf; Jan. 2013.

Luer Check Valve, Short Body; Halkey Roberts; http://www.halkeyroberts.com/products/medical/luer-activated-valves/luer-check-valve-short-body.aspx; 2009.

Needlefree Male Slip Luer Check Valve; Halkey Roberts; http://www.halkeyroberts.com/products/medical/luer-lock-access-valves/needlefree-male-slip-luer-check-valve.aspx; 2009.

* cited by examiner

SYSTEMS AND METHODS FOR MONITORING AN INJECTION PROCEDURE

BACKGROUND

The present disclosure relates generally to medical devices and, more particularly, to monitoring physiological parameters using an indicator dilution analysis.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical practitioners often desire to monitor certain physiological characteristics of their patients. Accordingly, a wide variety of devices have been developed for monitoring patient characteristics. Such devices provide doctors and other healthcare personnel with the information they need to provide healthcare for their patients. As a result, such monitoring devices have become an indispensable part of modem medicine. For example, clinicians may wish to monitor a patient's blood flow to assess cardiac function. In particular, clinicians may wish to monitor a patient's cardiac output. The determination of cardiac output may provide information useful for the diagnosis and treatment of various disease states or patient abnormalities. For example, in cases of pulmonary hypertension, a clinical response may include a decrease in cardiac output.

Accordingly, there are a variety of clinical techniques that may be used for analyzing cardiac output or other hemodynamic parameters. In one technique known as indicator dilution (e.g., thermodilution, indicator dye dilution, lithium dilution, etc.), an indicator, such as a dye or saline solution, is injected into a circulatory system of a patient, and information about certain hemodynamic parameters may be determined by assessing the dilution of the indicator after mixing with the bloodstream. For example, a measure of cardiac output may be determined based on a decrease in blood temperature over a period of time resulting from the injected indicator. In some instances, it may be desirable to determine the start and end time of the injection, which may be used in the calculation of cardiac output.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

Some embodiments described herein are directed to a sensor assembly. The sensor assembly may include a connector, which may include a first end configured to be coupled to an injection device configured to inject a fluid. The connector may also include a second end configured to be coupled to tubing configured to deliver the fluid to a patient such that the connector, when coupled, is between the tubing and the injection device. Further, the connector may include a lumen extending from the first end to the second end. The connector may also include a valve assembly configured to enable flow of the fluid through the lumen when the connector is in an open state and to reduce (e.g., stop) flow of the fluid through the lumen when the connector is in a closed state. Additionally, the sensor assembly may include a sensor disposed proximate to the connector and configured to generate a signal relating to whether the connector is in the open state or the closed state.

Other embodiments directed herein are directed to a system. The system may include a connector configured to interface between an injection device configured to inject a fluid and a catheter configured to deliver the fluid to a patient. The connector may include a lumen extending from a first end of the connector to a second end of the connector. Additionally, the connector may include a valve assembly configured to enable flow of the fluid through the lumen when the connector is in an open state and to reduce (e.g., stop) flow of the fluid through the lumen when the connector is in a closed state. The system may also include a sensor disposed proximate to the connector and configured to generate a signal relating to the state of the connector. Furthermore, the system may include a monitor including a processor configured to receive the signal from the sensor and to determine a start time and an end time of an injection procedure based at least in part upon the signal. The start time of the injection may be based at least in part upon a determination that the connector is in the open state and the end time of the injection may be based at least in part upon a determination that the connector is in the closed state.

Further embodiments described herein are directed to a method. The method may include using a processor to receive two or more signals from a sensor indicative of a state of a valve assembly. The state of the valve assembly may include an open state or a closed state. The method may also include using a processor to determine whether the valve assembly is in the open or closed state based at least in part upon the received signals. The method may include using a processor to determine a start time of an injection procedure based at least in part upon the determination that the valve assembly is in the open state. Furthermore, the method may include using a processor to determine an end time of the injection procedure based at least in part upon the determination that the open state of the valve assembly is followed by the closed state.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
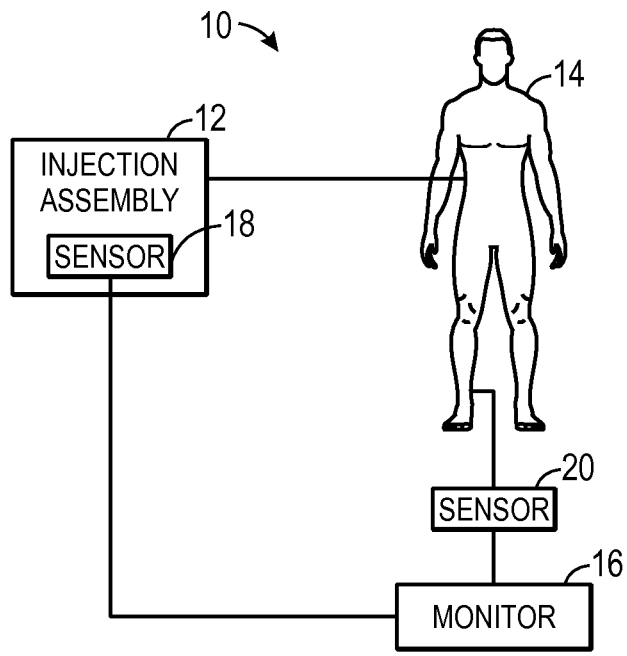
FIG. 1 is a schematic illustrating a system for implementing an indicator dilution technique, in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As noted above, cardiac output may be determined using several clinical techniques, such as indicator dilution (e.g., thermodilution, indicator dye dilution, lithium dilution, etc.). For example, for thermodilution techniques, a known volume of an indicator at a known temperature (e.g., a temperature higher or lower than the temperature of blood) may be injected into the blood stream of a patient via a catheter, and the temperature of blood downstream from the injection may be measured over time. In particular, a measure of cardiac output may be determined based on the temperature deviation of blood as a function of time resulting from the injected indicator. Accordingly, it may be desirable to determine the start and end time of the injection, which may be used in the calculation of cardiac output. However, it may be difficult to determine a precise start and end time of the injection.

To address these issues, the present embodiments describe systems and methods for determining the start time, end time, or duration of an injection. For example, a system may include an injection device (e.g., a syringe) for injecting a bolus (e.g., an indicator) into a patient. The system may also include a catheter coupled to the injection device for delivering the indicator to the patient. The system may also include one or more sensors, which may provide a signal related to an injection time, which may be provided to a downstream medical device that may utilize the signal to determine the start and/or end time of the injection. For example, in certain embodiments, the catheter may be coupled to the injection device via a connector, such as a pressure-activated luer check valve, and a sensor may be configured to provide information related to the state of the luer check valve (e.g., open or closed), which may be used by the downstream medical device to determine whether the injection device is delivering the indicator to the patient. In other embodiments, a sensor may be configured to provide information relating to a pressure change, temperature change, and/or a flow rate change resulting from the indicator. By providing information related to a status of the injection, the start and end time of the injection may be determined, which may increase the accuracy of various clinical measurements, such as cardiac output.

With the foregoing in mind, FIG. 1 depicts a schematic diagram of a system 10 for implementing indicator dilution techniques. The system 10 may be configured to implement transpulmonary thermodilution techniques, indicator dye dilution techniques, lithium dilution indicator dilution techniques, or other indicator dilution techniques. The system 10 may include an injection assembly 12 to deliver an indicator (e.g., a bolus of an indicator) to a patient 14. The injection assembly 12 may include any suitable components for delivering the indicator to the patient 14, such as one or more catheters, one or more injection devices (e.g., manual or automated syringes), one or more connectors (e.g., valves), and/or medical tubing. The system 10 may also include sensors configured to acquire signals from components of the system 10 and/or from the patient 14, which may be utilized by a downstream monitor 16 to determine various parameters, such as physiological parameters of the patient 14 and parameters relating to the indicator dilution process (e.g., the start and end time of an injection). For example, as will be described in more detail below, the injection assembly 12 may include one or more sensors 18 to monitor one or more parameters of the injection assembly 12. In particular, the sensor 18 provides a signal to the monitor 16 that relates to an injection time. In turn, the monitor 16 uses the injection time in indicator dilution determination as provided herein. Additionally, the system 10 may include one or more sensors 20 configured to measure physiological signals from the patient 14. For example, in certain embodiments, the one or more sensors 20 may include photoacoustic sensors, pulse oximetry sensors, or any other suitable sensor.

In certain embodiments, the one or more sensors 20 may be photoacoustic sensors configured to detect acoustic pressure signals from a blood vessel site. In particular, physiological parameters may be determined using photoacoustic analysis and an indicator dilution response using the methods discussed in U.S. Patent Publication No. 2013/0137959 and U.S. Patent Publication No. 2013/01371260, each incorporated by reference for all purposes as if fully set forth herein. For example, the sensor 20 may detect a first pressure signal from a first blood vessel site, and another sensor 20 may detect a second pressure signal from a second blood vessel site. The first and second pressure signals may be representative of a dilution response corresponding to one or more indicators that have been injected into the patient 14. The monitor 16 may be configured to derive physiological parameters based at least in part upon the first and the second pressure signals. For example, the physiological parameters may include cardiac output, intrathoracic blood volume, intrathoracic circulatory volume, global end-diastolic volume, pulmonary circulatory volume, extravascular lung water, and/or any other suitable physiological parameter.

Figure 2:
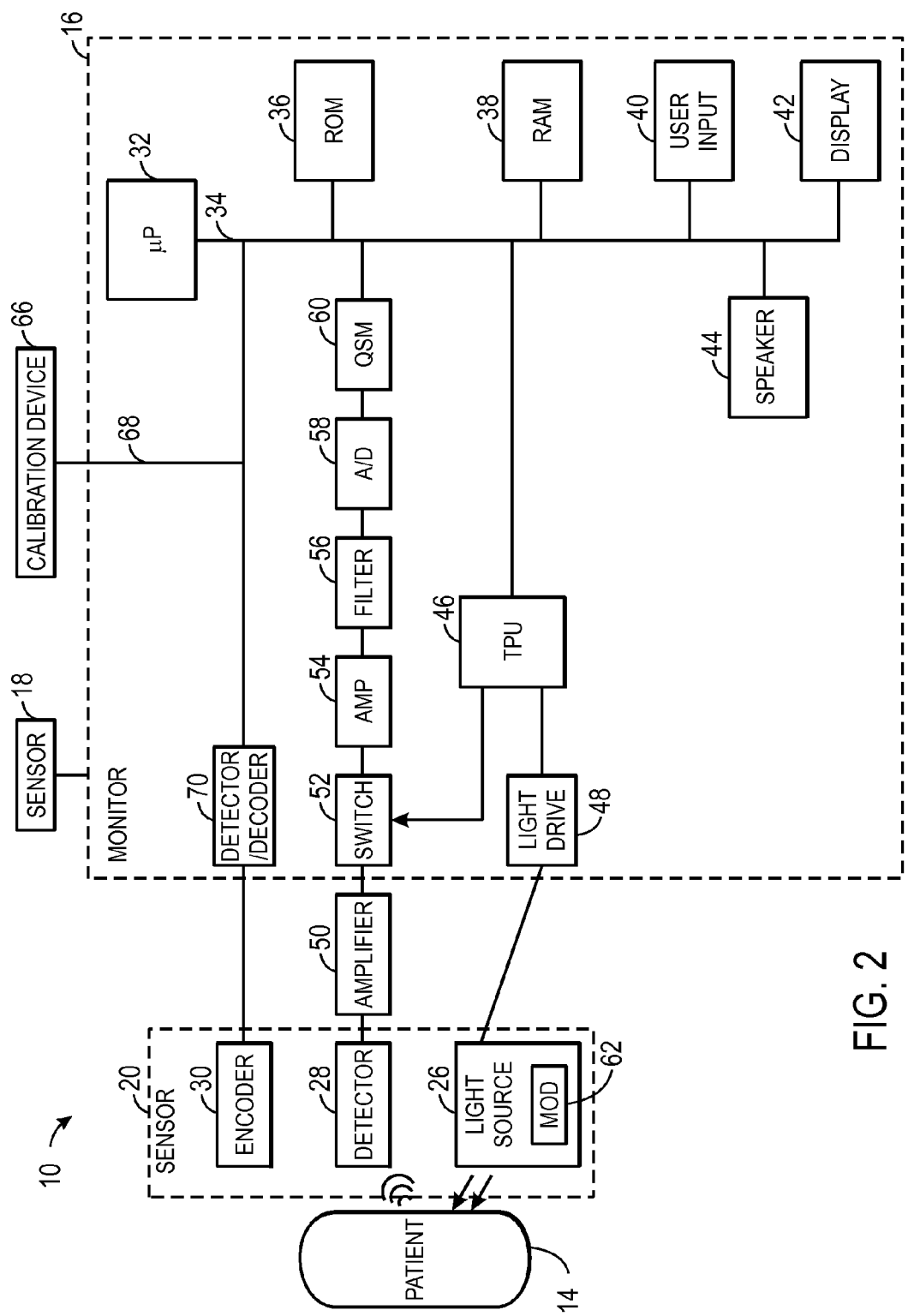
FIG. 2 is a block diagram illustrating components of the system of FIG. 1, in accordance with an embodiment.

FIG. 2 illustrates a block diagram of a physiological monitoring system, such as the system 10 of FIG. 1, which may be configured to determine physiological parameters of the patient 14. For example, the system 10 may be configured to determine physiological parameters of the patient 14 based at least in part upon signals received from photoacoustic sensors 20. Additionally, the system 10 may include additional sensors, such as the one or more sensors 18.

The sensor 20 may include a light source 26, a detector 28, and an encoder 30. In some embodiments, the light source 26 may be configured to emit one or more wavelengths of light (e.g., visible, infrared) into the patient's 14 tissue. Accordingly, light source 26 may provide red light, infrared (IR) light, any other suitable light, or any combination thereof, that may be used to calculate physiological parameters of the patient 14. In some embodiments, a red wavelength may be between about 600 nanometers (nm) and about 700 nm. In some embodiments, an IR wavelength may be between about 800 nm and about 1000 nm. In embodiments where a sensor array is used in place of a single sensor 20, each sensor 20 may be configured to provide light of a single wavelength. For example, a first sensor 20 may emit only red light while a second sensor 20 may emit only IR light. In a further example, the wavelengths of light used may be selected based on the specific location of the sensor 20.

It will be understood that, as used herein, the term "light" may refer to energy produced by electromagnetic radiation sources. Light may be of any suitable wavelength and intensity, and modulations thereof, in any suitable shape and direction. The detector 28 may be chosen to be specifically sensitive to the acoustic response of the patient's tissue arising from the use of the light source 26. It will also be understood that, as used herein, the "acoustic response" shall refer to pressure and changes thereof caused by a thermal response (e.g., expansion and contraction) of tissue to light absorption by the tissue of constituent thereof.

In some embodiments, the detector 28 may be configured to detect the acoustic response of tissue to the photonic excitation caused by the light source 26. In some embodiments, the detector 28 may be a piezoelectric transducer which may detect force and pressure and output an electrical signal via the piezoelectric effect. In some embodiments, the detector 28 may be a Fabry-Perot interferometer, or etalon. For example, a thin film (e.g., composed of a polymer) may be irradiated with reference light, which may be internally reflected by the film. Pressure fluctuations may modulate the film thickness, thus causing changes in the reference light reflection which may be measured and correlated with the acoustic pressure. In some embodiments, the detector 28 may convert the acoustic pressure signal into an electrical signal (e.g., using a piezoelectric material, photodetector of a Fabry-Perot interferometer, or other suitable device). After converting the received acoustic pressure signal to an electrical, optical, and/or wireless photoacoustic signal, the detector 28 may send the photoacoustic signal to the monitor 16, where physiological parameters may be calculated based on the photoacoustic activity within the tissue of the patient 14.

In some embodiments, the encoder 30 may contain information about the sensor 20, such as what type of sensor it is (e.g., where the sensor is intended to be placed on the patient 14), the wavelength(s) of light emitted by the light source 26, the intensity of light emitted by the light source 26 (e.g., output wattage or Joules), the mode of the light source 26 (e.g., pulsed versus continuous wave), or any other suitable information, or any combination thereof. This information may be used by the monitor 16 to select appropriate algorithms, lookup tables, and/or calibration coefficients stored in the monitor 16 for calculating physiological parameters of the patient 14.

Additionally, the encoder 30 may contain information specific to the patient 14, such as, for example the age, weight, and diagnosis of the patient 14. This information about the patient's characteristics may allow the monitor 16 to determine, for example, subject-specific threshold ranges in which the subject's physiological parameter measurements should fall and to enable or disable additional physiological parameter algorithms. The encoder 30 may, for instance, be a coded resistor that stores values corresponding to the type of sensor 20 or the type of each sensor in the sensor array, the wavelengths of light emitted by the light source 26 and/or each sensor of the sensor array, and/or the patient's characteristics.

In some embodiments, the encoder 30 may include a memory on which one or more of the following information may be stored for communication to the monitor 16; the type of sensor 20; the wavelengths of light emitted by the light source 26; the particular acoustic range that each sensor in the sensor array is monitoring; the particular acoustic spectral characteristics of the detector 28; a signal threshold for each sensor in the sensor array; any other suitable information; or any combination thereof.

In some embodiments, signals from the detector 28 and the encoder 30 may be transmitted to the monitor 16. In the embodiment shown, the monitor 16 may include a general-purpose processor 32 connected to an internal bus 34. The processor 32 may be adapted to execute software, which may include an operating system and one or more applications, as part of performing the functions described herein. Also connected to the bus 34 may be a read-only memory (ROM) 36, a random access memory (RAM) 38, any other type of non-volatile storage such as flash, user inputs 40, display 42, and speaker 44.

The ROM 36 and RAM 38 are illustrated by way of example, and not limitation. Any suitable computer-readable media may be used in the system for data storage. Computer-readable media are capable of storing information that can be interpreted by processor 32. This information may be data or may take the form of computer-executable instructions, such as software applications, that cause the processor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 46 may provide timing control signals to light drive circuitry 48, which may control the activation of the light source 26. For example, the TPU 46 may control pulse timing (e.g., pulse duration and inter-pulse interval) for a time domain photoacoustic (TD-PA) monitoring system. The TPU 46 may also control the gating-in of signals from the detector 28 through an amplifier 50 and switching circuit 52. The received signal from the detector 28 may be passed through an amplifier 54, a low pass filter 56, and an analog-to-digital converter 58. The digital data may then be stored in a queued serial module (QSM) 60 (or buffer) for later downloading to the RAM 38 as QSM 60 is filled. In some embodiments, there may be multiple separate parallel paths having components equivalent to the amplifier 54, filter 56, and/or A/D converter 58 for multiple light wavelengths or spectra received. Any suitable combination of components (e.g., the processor 32, the RAM 38, the analog to digital converter 58, any other suitable component shown or not shown in FIG. 2) coupled by bus 34 or otherwise coupled (e.g., via an external bus), may be referred to as "processing equipment."

In the embodiment shown, the light source 26 may include a modulator 62, in order to, for example, perform frequency domain photoacoustic (FD-PA) analysis. The modulator 62 may be configured to provide intensity modulation, spatial modulation, any other suitable optical signal modulations, or any combination thereof. For example, the light source 26 may be a CW light source, and the modulator 62 may provide intensity modulation of the CW light source such as using a linear sweep modulation. In some embodiments, the modulator 62 may be included in the light drive 48, or other suitable components of the system 10, or any combination thereof.

A calibration device 66, which may be powered by the monitor 16 via a communicative coupling 68, a battery, or by a conventional power source such as a wall outlet, may include any suitable signal calibration device. The calibration device 66 may be communicatively coupled to the monitor 16 via communicative coupling 68, and/or may communicate wirelessly (not shown). In some embodiments, the calibration device 66 is completely integrated within the monitor 16. In some embodiments, the calibration device 66 may include a manual input device (not shown) used by an operator to manually input reference signal measurements obtained from some other source (e.g., an external invasive or non-invasive physiological measurement system).

In some embodiments, the processor 32 may determine the patient's physiological parameters, such as blood oxygen saturation, mixed venous oxygen saturation ($SvO_2$), oxy-hemoglobin concentration, deoxy-hemoglobin concentration, total hemoglobin concentration (tHb), pulse rate, cardiac output, intrathoracic blood volume, intrathoracic circulatory volume, global end-diastolic volume, pulmonary circulatory volume, extravascular lung water, and/or other physiological parameters, using various algorithms and/or lookup tables based on the value of the received signals and/or data corresponding to the acoustic response received by the detector 28. Signals corresponding to information about the patient 14, and particularly about the acoustic signals emanating from the patient's tissue over time, may be transmitted from the encoder 30 to a decoder 70. These signals may include, for example, encoded information relating to subject characteristics. The decoder 70 may translate these signals to enable the processor 32 to determine the thresholds based at least in part on algorithms or lookup tables stored in the ROM 36. In some embodiments, the user inputs 40 may be used to enter information, select one or more options, provide a response, provide input settings, provide any other suitable inputting function, or any combination thereof. The user inputs 40 may be used to enter information about the patient 14 such as, for example, age, weight, height, diagnosis, medications, treatments, and so forth. In some embodiments, the display 42 may exhibit a list of values, which may generally apply to the patient 14, such as, for example, age ranges or medication families, which the user may select using user inputs 42.

In addition to determining the patient's physiological parameters, the processor 32 may also determine one or more parameters relating to the system 10 using various algorithms and/or lookup tables based on the value of the received signals and/or data corresponding to the acoustic response from the detector 28. For example, the processor 32 may be configured to determine the start time, end time, and/or duration of an injection of the indictor dilution procedure. In particular, the processor 32 may analyze changes in the acoustic response from the detector 28, which may be caused by introduction of a bolus of an indicator in the patient 14. A bolus dose of an indicator may cause the properties at a photoacoustic monitoring site to change in time as the bolus dose passes the site. Introduction of the indicator may alter one or more properties of the blood that interacts with the indicator (e.g., blood near the bolus dose). The system 10 may monitor the blood (e.g., hemoglobin) rather than the indicator, to detect dilution. In a further example, an indicator having a temperature different from the temperature of the patient's un-dosed blood may be introduced into the patient's bloodstream (e.g., a "hot" or "cold" indicator, relative to the blood temperature). The system 10 may monitor the bloodstream temperature at the monitoring site, or the combined effects of hemo-dilution and thermo-dilution achieved by the bolus dose. In some embodiments, an indicator may have more than one property that may be distinguished from the patient's blood. For example, a cold dye indicator may be introduced to the patient's bloodstream, which may allow hemo-dilution and thermo-dilution effects to be detected. In some embodiments, more than one indicator may be introduced to the patient's bloodstream, each indicator having particular properties that may be unique relative to the other indicators. For example, an isotonic indicator or a hypertonic indicator may be introduced into the patient's bloodstream. In a further example, a cold isotonic indicator and a dye indicator may be introduced into the patient's bloodstream. An indicator may include saline (e.g., isotonic, hypertonic, hypotonic), dye (e.g., indocyanine), lithium, any other suitable chemical or mixture, or any combination thereof.

Figure 3:
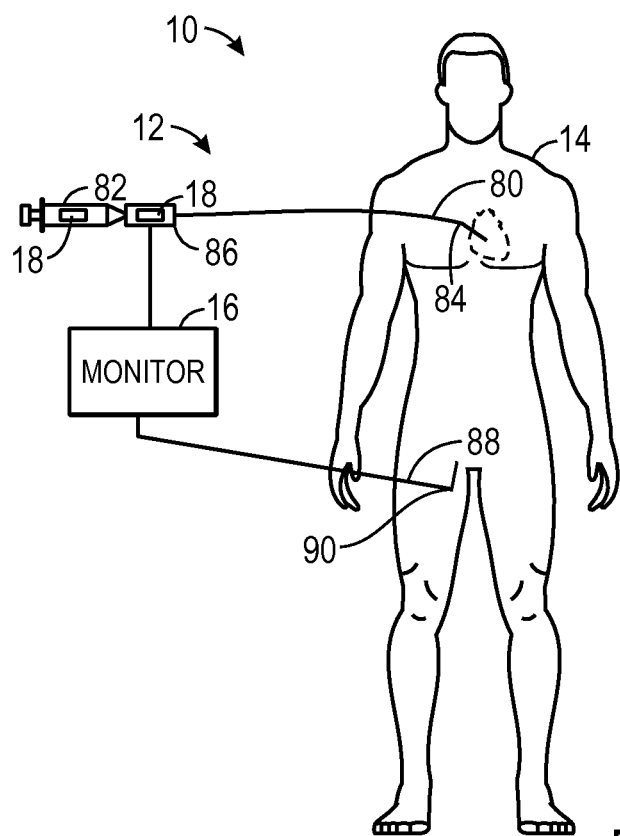
FIG. 3 is a schematic illustrating a system for implementing an indicator dilution technique including a monitor, one or more catheters, an injection device, and one or more sensors, in accordance with an embodiment.

As noted above, the system 10 may additionally or alternatively monitor parameters of the system (e.g., the start and end time of an injection) based on signals received from sensors 18 of the injection assembly 12. While FIG. 2 illustrates a non-invasive technique for monitoring indicator dilution, the injection assembly 12 may also be used in conjunction with invasive indicator dilution techniques. For example, FIG. 3 depicts a schematic diagram of the system 10 including the injection assembly 12 and the sensors 18, in which the injection assembly 12 of the system 10 is coupled to a catheter 80, which may be configured to enter an artery or vein of the patient 14, and an injection device 82, which may be configured to deliver a bolus of an indicator to the patient 14 via the catheter 80. The catheter 80 may be a central venous catheter or a peripherally inserted central catheter (e.g., a PICC line). In certain embodiments, the catheter 80 may include one or more sensors 84, such as pressure and/or temperature sensors, for measuring physiological parameters of the patient 14. Accordingly, the sensors 84 of the catheter 80 may be operatively coupled to the monitor 16 via cables or a wireless transceiver. The catheter 80 may be coupled to the injection device 82 via a connector 86 (e.g., a valve, a port, a luer taper, etc.) and, in some embodiments, via medical tubing.

The injection device 82 may deliver a bolus of an indicator to the patient 14 via the catheter 80. In particular, the injection device 82 may be configured to deliver a bolus that may have a predetermined volume and/or a predetermined temperature. In some embodiments, the injection device 82 may be manually operated by a user. In other embodiments, the injection device 82 may include a drive mechanism, such as a motor, which may be controlled by the injection device 82 and/or another medical device, such as the monitor 16.

As noted above, for thermodilution measurements, the temperature of blood downstream from the injection site may be monitored invasively and may be used in the determination of various physiological parameters of the patient 14. Accordingly, in some embodiments, the system 10 may also include a catheter 88, which may be configured to be inserted into an artery downstream from the catheter 80. For example, the catheter 88 may be inserted into a peripheral artery, such as an axillary artery, radial artery, or femoral artery. Similar to the catheter 80, the catheter 88 may include one or more sensors 90, such as a temperature sensor and/or a pressure sensor, for measuring physiological parameters of the patient 14.

As noted above, the injection assembly 12 may include one or more sensors 18 for detecting changes in the injection assembly 12, which may be utilized by the processor 32 to determine the start and end time of the injection. The sensors 18 of the injection assembly 12 may include optical sensors, electromagnetic induction sensors, radio-frequency identification sensors, pressure sensors, temperature sensors, flow rate sensors, or any other suitable sensor for detecting changes in the injection assembly 12. In some embodiments, the injection device 82 may include one or more of the sensors 18 for measuring parameters of the indicator before, during, and/or after the indicator is injected into the patient 14. Additionally or alternatively, one or more sensors 18 may be disposed about or proximate to the connector 86 of the injection assembly 12. In particular, as will be described in more detail below, the sensors 18 disposed about the connector 86 may be configured to generate signals relating to the state of the connector 86, such as open to allow flow of the indicator or closed to reduce (e.g., stop, block, or prevent) flow the indicator. It should be understood that the sensors 18 may each be a separate assembly or an assembly including multiple sensors disposed generally adjacent to and/or on any components of the injection assembly 12 (e.g., the catheter 80, the injection device 82, the connector 86, the catheter 88, and/or any medical tubing of the injection assembly 12), or may be integral with the any components of the injection assembly 12.

In certain embodiments, the injection assembly 12 may include an adapter, e.g., the connector 86, that houses the sensor 18 in a unitary assembly. Such an embodiment may be advantageous for adapting existing injection components for use with the present techniques. For example, the injection device 82 may be directly coupled to the connector 86, which in turn is coupled to the appropriate medical tubing or catheter 80. In this manner, the connector 86 interfaces between the injection device 82 and the tubing that delivers the bolus to the patient 14. Accordingly, in certain embodiments, the connector 86 is easily removable from and/or coupled to the injection device 82 by an operator. Further, the injection device 82 may also be configured to directly couple to the tubing in situations in which the connector 86 is not used.

Figure 4:
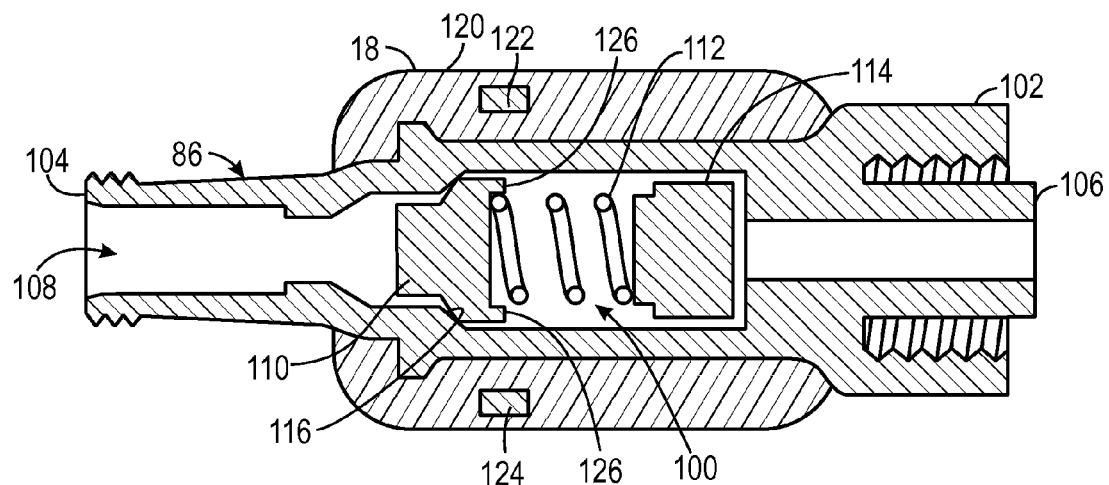
FIG. 4 is a cross-sectional view of a connector in a closed position and an optical sensor, in accordance with an embodiment.

Accordingly, the connector 86 may mimic the connection of the injection device to the tubing to act as an interface between these components in embodiments when the connector 86 is in use. In one embodiment, shown in FIG. 4, the connector 86 includes one or more sensors 18 configured to acquire measurements relating to a state (e.g., opened or closed) of a valve assembly 100 of the connector 86 disposed between the injection device 82 and the catheter 80, as illustrated in FIG. 4.

The connector 86 may include a housing 102 configured to house the valve assembly 100. The housing 102 may be made of any suitable material, such as polyvinyl chloride (PVC), polycarbonate, polypropylene, and/or acrylonitrile butadiene styrene (ABS). The connector 86 may include a luer female connector, such as a pressure activated luer check valve at first mating end 104 (e.g., an inlet) that is configured to mate with a male luer connector on the injection device 82. In addition, the connector 86 may include a second mating end 106 (e.g., an outlet) that is a male luer connector (i.e., analogous to the injection device 82 connection) and that couples to the tubing via a connector that accepts a male luer connector. In other embodiments, the first mating end 104 may be a male luer connector and/or the second mating end 106 may be a female luer connector. Further, in other embodiments, the mating ends 104 and 106 may be specialty connectors that only couple to a system configured with complementary mating connectors on the injection device 82 and tubing. Further, although the connector 86 may be configured to be removable from the injection device 82, the connector 86 may also be implemented as attached to or unitary with the injection device.

The connector 86 also includes a passageway 108 disposed between the first and the second mating ends 104 and 106. In some embodiments, the first mating end 104 may be configured to securely mate with (e.g., form a tight seal) the injection device 82 or any other suitable syringe, catheter, and/or tubing. Additionally, in some embodiments, the second mating end 106 may be configured to securely mate with the catheter 80 or any other suitable syringe, catheter, and/or tubing. The first and second mating ends 104 and 106 may be male or female and may be threaded or configured for a friction fit.

In certain embodiments, the valve assembly 100 may be initially biased in a closed position such that the indicator may not flow through the passageway 108 (e.g., a lumen) of the connector 86. In particular, the valve assembly 100 may include a valve stem 110, a biasing member 112 (e.g., a spring), and a valve plug 114, each of which may be disposed in the passageway 108. The valve stem 110 may be made of any suitable gasket material, such as silicone, metal, rubber, polypropylene, or combinations thereof. The biasing member 112 may be formed from any suitable material, such as a metal (e.g., stainless steel). Additionally, the valve plug 114 may be made of any suitable gasket material, such as polypropylene, silicone, rubber, or combinations thereof.

In the closed position, as illustrated in FIG. 4, the valve stem 110 may be sealably engaged to internal surfaces 116 of the housing 102 to block or reduce the flow of the indicator through the passageway 108. The valve stem 110 may be any shape suitable for blocking or reducing the flow of the indicator through the passageway 108. For example, the valve stem 110 may be generally cylindrical or rectangular with a tapered diameter and/or a stepped diameter. In other embodiments, the valve stem 110 may be generally spherical. As will be described in more detail in FIG. 5, the valve stem 110 may be laterally (e.g., axially) displaced by the injection of the indicator (e.g., above a predetermined pressure) and/or by the insertion of the injection device 82 into the first mating end 104, which may compress the biasing member 112 and actuate the valve assembly 100 into the open position such that the indicator may flow through the passageway 108 and exit through the second mating end 106.

In certain embodiments, the sensor 18 may be configured to acquire measurements relating to a position of the valve stem 110, which may be transmitted to the monitor 16 for use in determining whether the indicator is being delivered to the patient. In one embodiment, the sensor 18 may be an optical sensor 120 including at least one emitter 122 and at least one detector 124, which may generate a signal related to detected light. For example, in one embodiment, the emitter 122 may include one, two, or more light emitting components (such as light emitting diodes or LEDs) adapted to transmit light at one or more specified wavelengths. In certain embodiments, the emitter 122 may include a laser diode or a vertical cavity surface emitting laser (VCSEL). The laser diode may be a tunable laser, such that a single diode may be tuned to various wavelengths, which may be selected based at least in part upon a color and/or opacity of the housing 102 of the connector 86, components of the valve assembly 100 (e.g., the valve stem 110), and/or the indicator, as will be discussed in more detail below. That is, the light may be any suitable wavelength or wavelengths (such as a wavelength between about 500 nm to about 1000 nm or between about 600 nm to about 900 nm) that is capable of penetrating the housing 102 of the connector 86 and is absorbed by the valve stem 110 and/or other target component. The detector 124 may be a photodetector, such as a silicon photodiode package, selected to receive light in the range emitted from the emitter 122. While the illustrated embodiment shows the emitter 122 and the detector 124 in a transmission-type arrangement, the emitter 122 and the detector 124 may also be configured to operate in a reflectance-type arrangement.

In such an embodiment, the lateral displacement of the valve stem 110 may move within an optical path of the optical sensor 120 or may move generally out of an optical path of the optical sensor 120. To amplify a difference in light intensity of signals acquired when the valve stem 110 is within the optical path of the optical sensor 120 and when the valve stem 110 is outside of the optical path of the optical sensor 120, the housing 102 (and any other components that may surround the valve stem 110) may be clear or at least partially transparent, such that components of the valve assembly 100, such as the valve stem 110, may be visible through the housing 102. In this manner, the wavelength(s) emitted from the emitter 122 may penetrate the housing 102 more easily with reduced absorption. Additionally, the valve stem 110 may be opaque or at least more opaque than the housing 102. Thus, when the valve stem 110 moves within the optical path, the valve stem 110 may block light emitted from the emitter 122 from reaching the detector 124, while light emitted from the emitter 122 may generally reach the detector 124 when the valve stem 110 is outside of the optical path.

The biasing member 112 may have any suitable stiffness that enables the valve stem 110 to move within the optical path when the indicator is injected through the connector 86. In some embodiments, the biasing member 112 may be a spring and may have a spring constant that enables the valve stem 110 to move between approximately 1 centimeter to 10 centimeters, 2 centimeters to 7 centimeters, or 3 centimeters to 5 centimeters within the valve assembly 100. An appropriate spring constant may be determined based at least in part upon an average pressure of an injection, which may be estimated, determined using empirical data, or predetermined using an automatic injection device 82.

To differentiate between the open and closed position of the valve assembly 100, the optical sensor 120 may be positioned about the valve assembly 100 such that the optical path does not pass through the valve stem 110 when the valve assembly 100 is in the open position and the optical path passes through the valve stem 110 when in the closed position or vice versa. As illustrated, the optical sensor 120 is positioned about the valve assembly 100 such that the emitter 122 and the detector 124 are disposed proximate to an edge 126 of the valve stem 110. As such, the valve stem 110 does not block the optical path when the valve assembly 100 is in the closed position. In this manner, the optical sensor 120 may detect a change in the optical path resulting from the initial movement of the valve stem 110, which may indicate the start of an injection procedure. In other embodiments, the emitter 122 may be disposed within or on the valve stem 110 and the detector 126 may be disposed in a housing of the optical sensor 120. Alternatively, the detector 126 may be disposed within or on the valve stem 110 and the emitter 122 may be disposed in the housing of the optical sensor 120. In this manner, the emitter 122 or the detector 126 may move with the valve stem 110 in and/or out of the path of the stationary detector 126 or emitter 122.

Figure 5:
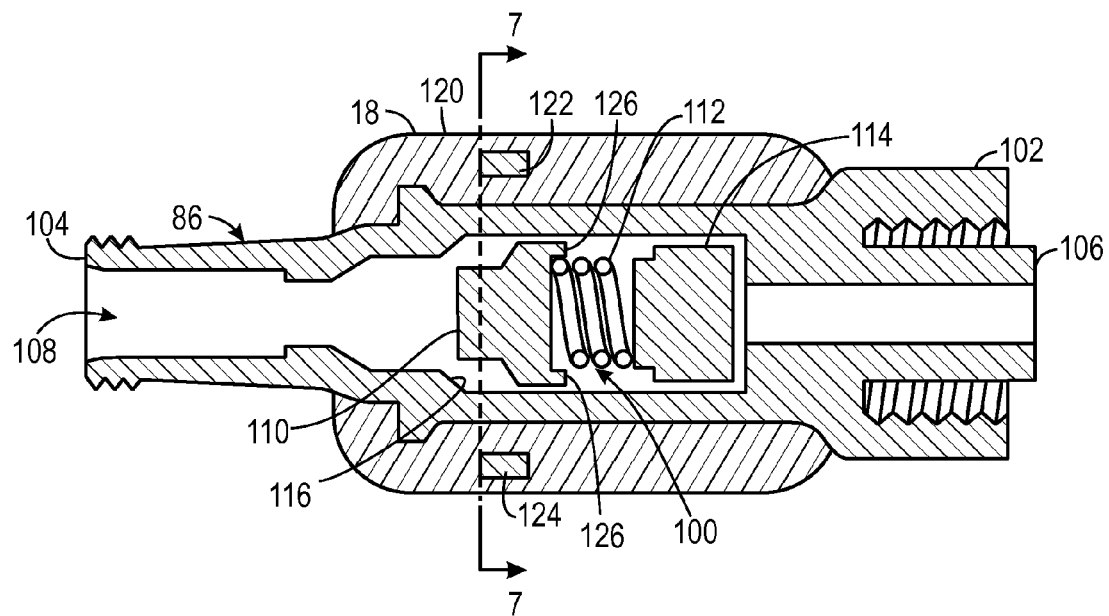
FIG. 5 is a cross-sectional view of the connector of FIG. 4 in an open position, in accordance with an embodiment.

As illustrated in FIG. 5, the optical path may be blocked by the valve stem 110 when the valve assembly 100 is in the open position. In particular, as noted above, pressure from the indicator injection may laterally displace the valve stem 110 causing the valve stem 110 to enter the optical path of the optical sensor 120. The lateral displacement of the valve stem 110 may enable the indicator to flow through the passageway 108 via apertures 128 between the valve stem 110 and the housing 102. The indicator may exit the second mating end 106 through the valve plug 114 (e.g., through fins of the valve plug 114). Accordingly, when the injection of the indicator ends and the valve stem 110 is no longer exposed to a pressure from the indicator, the biasing member 112 may uncompress and cause the valve stem 110 to return to the closed position such that the optical path is not blocked by the valve stem 110. In this manner, the optical sensor 120 may detect a change in the optical path resulting from the movement of the valve stem 110, which may indicate the end of an injection procedure.

To determine the start and end time of the injection, the optical sensor 120 may transmit the acquired signals to the monitor 16 for processing. In one embodiment, the optical sensor 120 may be coupled to the monitor 16 via a cable. In other embodiments, the optical sensor 120 may be configured to communicate wirelessly with the monitor 16. The processor 32 of the monitor 16 may be configured to determine the start and end time of the injection based at least in part upon a determined position of the valve stem 110 of the valve assembly 100, which may be determined using signals received from the optical sensor 120. For example, the processor 32 may compare the light intensity of a signal received from the optical sensor 120 to a minimum light intensity threshold indicative of a blocked optical path and may determine that the valve stem 110 is in the open position in response to determining that the light intensity is below the minimum light intensity threshold. Additionally or alternatively, the processor 32 may compare the light intensity of a signal received from the optical sensor 120 to the minimum light intensity threshold indicative of a blocked optical path and may determine that the valve stem 110 is in the open position in response to determining that the light intensity if above the minimum light intensity threshold. Further, in some embodiments, the processor 32 may compare the light intensity of the optical sensor 120 signal to a light intensity threshold indicative of an unblocked optical path. Accordingly, the processor 32 may determine that the valve stem 110 is in the open position if the light intensity is below the light intensity threshold and may determine that the valve stem 110 is in the closed position if the light intensity is above the light intensity threshold. As will be appreciated, in embodiments in which the optical sensor 120 is positioned about the valve assembly 100 such that the optical path is blocked by the valve stem 110 when the valve stem 110 is in the closed position and is not blocked when the valve stem 110 is in the open position, the processor 32 may compare the light intensity of a signal received from the optical sensor 120 to the minimum light intensity threshold indicative of a blocked optical path and may determine that the valve stem 110 is in the closed position if the light intensity is below the minimum light intensity threshold.

The processor 32 may be configured to determine the start and end time of an injection based at least in part upon information relating to the determined position of the valve stem 110. For example, the processor 32 may know that an injection procedure has started if the processor 32 determines that optical path has changed and the valve stem 110 has been displaced into the open position. In certain embodiments, the optical sensor 120 may acquire a baseline signal prior to the start of the injection. This baseline signal may be used by the processor 32 to detect a change in the optical path resulting from movement of the valve stem 110. The processor 32 may determine that the injection device 82 is delivering the indicator to the patient for the duration that the light intensity of the signal acquired by the optical sensor 120 is below the minimum light intensity threshold indicative of a blocked optical path. Further, the processor 32 may determine that the injection procedure is completed (e.g., the injection device 82 is not delivering the indicator to the patient) in response to a subsequent change in optical path after the determination that the valve stem 110 is in the opened position and a determination that the valve stem 110 is in the closed position.

Figure 6:
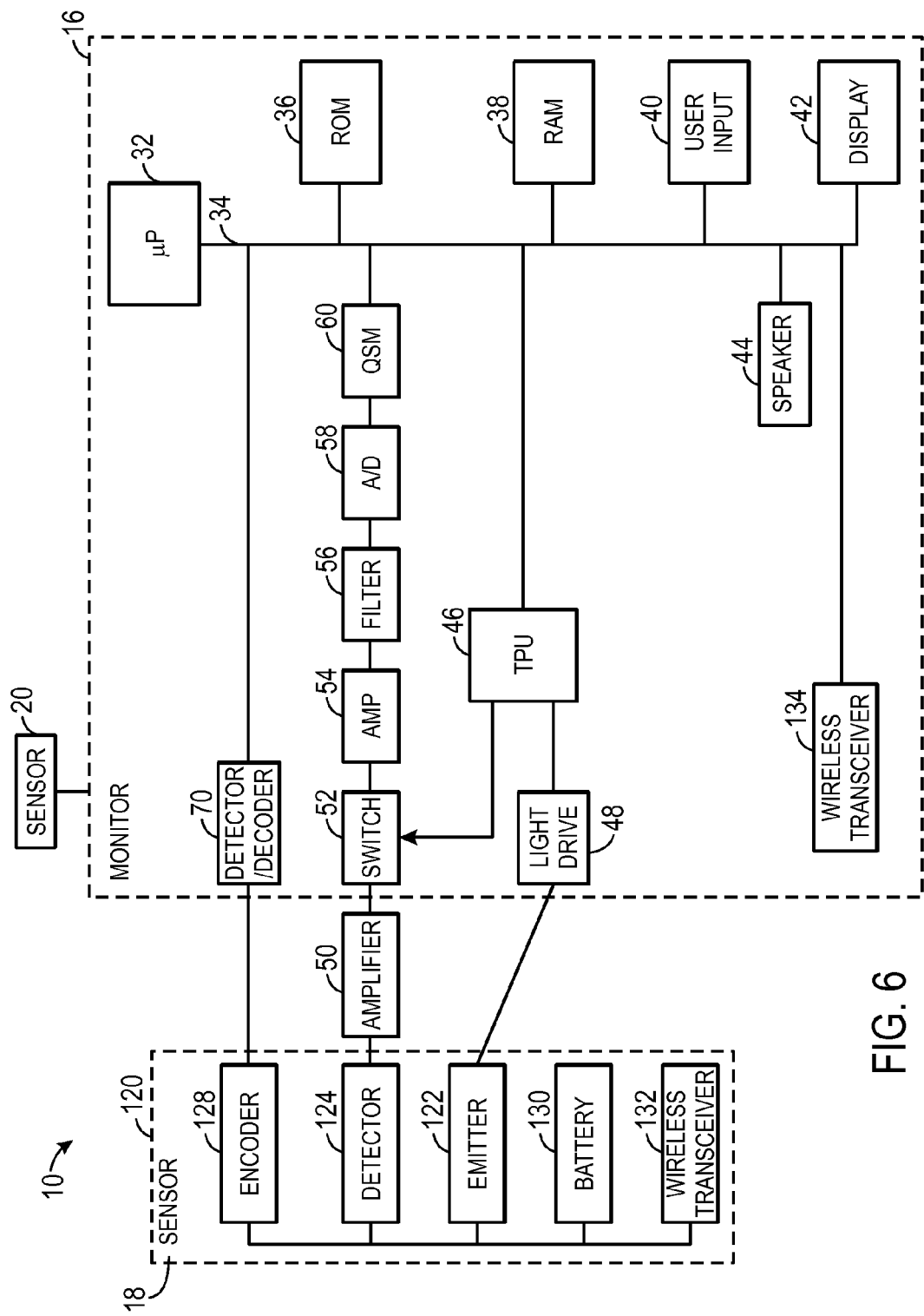
FIG. 6 is a block diagram, in accordance with an embodiment.

The thresholds and/or algorithms for determining the start and end time of the injection may be stored in the ROM 36 and/or the RAM 38 of the monitor 16. Additionally or alternatively, the thresholds and/or algorithms may be stored in a memory or other data encoding component of the optical sensor 120, such as an encoder 128, as shown in FIG. 6. For example, the encoder 128 may be a solid state memory, a resistor, or combination of resistors and/or memory components that may be read or decoded by the monitor 16, such as via the decoder 70 (or, optionally, via another decoder), to provide the monitor 16 with information about the attached optical sensor 120. For example, the encoder 128 may encode information about the optical sensor 120 or its components (such as information about the emitter 122 and/or the detector 124). Such encoded information may include information about the type of emitter(s) 122 present on the optical sensor 120, information about the wavelengths which the emitter 122 is capable of emitting, and the properties and/or detection range of the detector 124. The encoded information may also include information about the configuration or location of the optical sensor 120, the emitter 122, and the detector 124 relative to components of the valve assembly 100 (e.g., the valve stem 110). For example, the encoded information may include an indication that the optical sensor 120 is intended to be positioned about the valve assembly 100 such that the optical path is unblocked when valve stem 110 is in the closed position and is blocked when the valve stem 110 is in the open position, or vice versa. This information may allow the monitor 16 to select appropriate algorithms and/or calibration coefficients for calculating the start and end time of an injection and for determining whether the optical sensor 120 is correctly positioned about the valve assembly 100.

In certain embodiments, the optical sensor 120 (and other embodiments of the sensors 18) may include a battery 130 for powering the emitter 122, the detector 124, and any other components that may be present in the optical sensor 120, such as a data processing circuitry (e.g., a processor, an application specific integrated circuit, or so forth) and/or a wireless transceiver 132, which may be configured to wirelessly communicate with a wireless transceiver 134 of the monitor 16. Additionally or alternatively, the optical sensor 120 may include a power generating device (not shown) and/or a power cable (not shown) for receiving wired power from an external power source (e.g., the monitor 16). In certain embodiments, the optical sensor 120 may include a light drive (not shown) for driving the emitter 122. Alternatively, the TPU 46 of the monitor 16 may provide timing control signals to the light drive circuitry 48, which may control the operation of the emitter 122, such as to control when, for how long, and/or how frequently the emitter 122 is activated, and if multiple light sources are used, the multiplexed timing for the different light sources.

Figure 7:
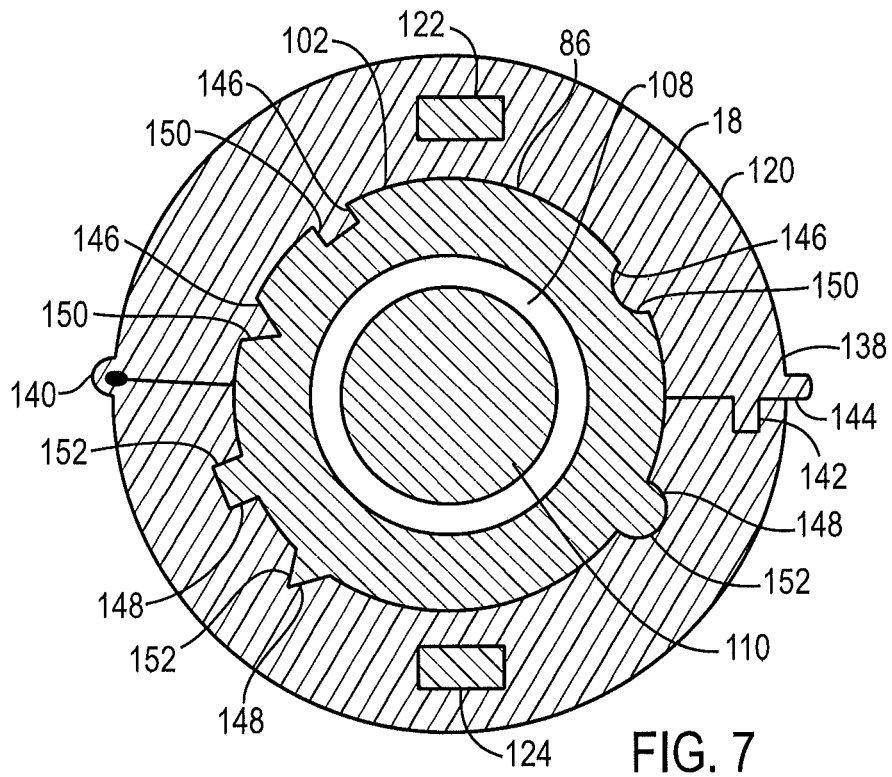
FIG. 7 is a cross-sectional view of the connector of FIG. 5 in an open position taken along line 7-7 of FIG. 5, in accordance with an embodiment.

The optical sensor 120 may also include a housing 138 (e.g., a sensor body), as shown in FIG. 7, which illustrates a cross-sectional view of the connector 86 and the optical sensor 120 taken along line 7-7 of FIG. 5. The housing 138 may be generally configured to protect the components of the optical sensor 120. The housing 138 may take any suitable form and may be formed from any suitable materials. For example, in some embodiments, the housing 138 may be formed from plastic or metal materials, or any combination thereof. In some embodiments, the housing 138 may include features for ambient light protection. For example, the housing 138 may be opaque or may have a colored interior surface (e.g., dyed, painted, pigmented, etc.) configured to absorb light that enters the housing 138. The housing 138 may thus reduce the amount of ambient light that reaches the detector 124 and, thus, may reduce the amount of ambient light interference in the acquired signals. While the housing 138 is illustrated as having a generally circular cross-section, the housing 138 may be formed in any suitable shape and may be uniform or non-uniform in cross-section about its length.

In some embodiments, the housing 138 may be configured to position the optical sensor 120 about the connector 86. For example, the connector 86 may be configured to be slidably inserted into the housing 138, and the housing 138 may be secured to at least a portion of the connector 86 via a friction fit. Further, the housing 138 may be formed from a silicone material, and an inside diameter of the housing 138 may expand to fit the connector 86. In other embodiments, the housing 138 may include a hinge 140 and an engagement mechanism 142, which may enable the housing 138 to open and close about the connector 86. The engagement mechanism 142 may include a tab 144 and/or a button to enable a user to more easily open the housing 138. For example, the housing 138 may be a clam shell assembly or a clip.

Providing the hinge 140 and the engagement mechanism 142, or other embodiment of the housing 138 that enables the housing 138 to be easily removed from the connector 86, may be desirable in certain circumstances. For example, providing a removable housing 138 may enable the optical sensor 120 to be reused and/or remanufactured (e.g., to reuse at least the emitter 122 and the detector 124 in another sensor), while the connector 86 may be discarded after use. It may be desirable to reuse the optical sensor 120 to reduce costs. In other embodiments, the optical sensor 120 may be integrated in or on interior walls of the connector 86 and may not be removable. However, the connector 86 may be disposable, because the connector 86 may be exposed to patient fluids and may be difficult to disinfect. In some embodiments, the connector 86 may also be reused or remanufactured.

Additionally, the housing 138 may be configured to position the optical sensor 120 about the valve assembly 100. That is, a user may experience difficulty in aligning the emitter 122 and the detector 124 such that the optical path is not blocked by the valve stem 110 in the closed position and is blocked by the valve stem 110 in the open position (or vice versa). Accordingly, the housing 138 may include one or more features, which may enable the optical sensor 120 to be positioned about the connector 86 in only one location and/or orientation. In this manner, the housing 138 may reduce the chance of a user misplacing the optical sensor 120 relative to the valve assembly 100. For example, in some embodiments, the housing 138 of the optical sensor 120 and/or the housing 102 of the connector 86 may include one or more features to facilitate the positioning of the optical sensor 120 about the connector 86. For example, the housing 138 may include one more projections 146 or grooves 148 shaped to fit into one or more respective grooves 150 or projections 152 of the housing 102. The projections 146 and 152 and the grooves 148 and 150 may be positioned at any suitable location of the housing 138 and the housing 102, respectively. In some embodiments, the housing 138 may not include the projections 146 or grooves 148. In one embodiment, the housing 102 may include at least one pair of projections (not shown), which may be disposed on the housing 102 with an axial distance from one another that is approximately equal to the length of the housing 138 of the optical sensor 120. In this manner, when the optical sensor 120 is disposed about the connector 86, the pair of projections may be disposed proximate to the axial edges of the housing 138 of the optical sensor 120, which may reduce movement (e.g., axial or lateral sliding) of the optical sensor 120 relative to the connector 86.

The housing 138 may additionally include alignment indicia to provide information to a user regarding the proper placement of the optical sensor 120 about the connector 86. For example, the housing 138 may include one or more arrows, symbols, lines, numbers, text, or the like to facilitate the positioning of the optical sensor 120 about the connector 86. In some embodiments, the alignment indicia may indicate the positioning of the emitter 122 and the detector 124 about the valve stem 110.

Figure 8:
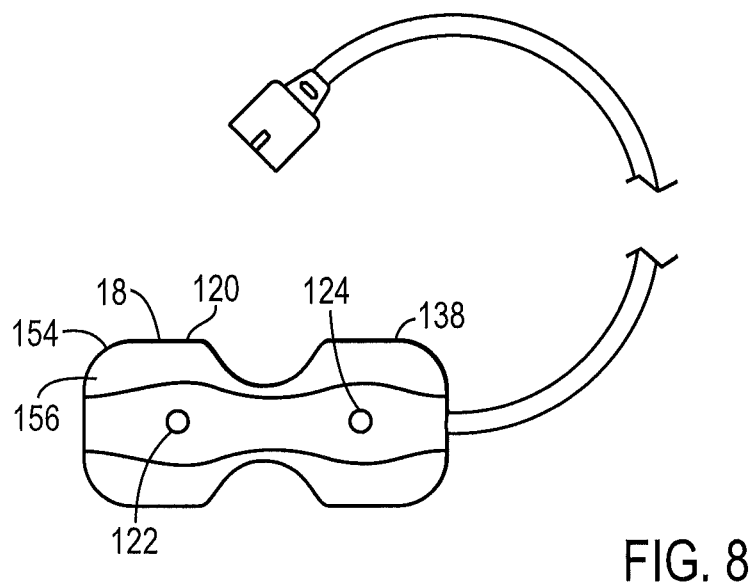
FIG. 8 is a perspective view of a sensor, in accordance with an embodiment.

In some embodiments, the optical sensor 120 may be an off-the-shelf sensor 154, as shown in FIG. 8. For example, the optical sensor 120 may be a pulse oximetry sensor or a regional oximetry sensor, such as those available from Covidien LP. In such embodiments, the optical sensor 120 may plug into the monitor 16 via a sensor connector port or with a monitor that is configured to receive pulse oximetry signals. The off-the-shelf optical sensor 154 may include the emitter 122, the detector 124, and the housing 138. In certain embodiments, the off-the-shelf optical sensor 154 may also include the encoder 128, the battery 130, and/or the wireless transceiver 132. The off-the-shelf optical sensor 154 may be a reusable, partially reusable, or disposable sensor and may be configured for reflectance and/or transmission operation. In some embodiments, the off-the-shelf sensor 120 may be a bandage-type sensor, which may be configured to at least partially wrap around the connector 86. Additionally, the off-the-shelf optical sensor 154 may include an adhesive layer 156 on the housing 138, which may be used to secure the off-the-shelf optical sensor 154 about the connector 86. In embodiments in which the off-the-shelf optical sensor 154 does not include an adhesive layer, one or more fasteners (e.g., a rubber band, Velcro®, plastic ties and/or straps, etc.) may be provided to secure the off-the-shelf optical sensor 154 about the connector 86.

In one embodiment, the optical sensor 120 may be a remanufactured off-the-shelf sensor. For example, the optical sensor 120 may be a remanufactured pulse oximetry sensor or a regional oximetry sensor, such as those available from Covidien LP. The optical sensor 120 may be remanufactured to at least include the emitter and the detector of a used off-the-shelf sensor. In some embodiments, the housing (e.g., sensor body) and/or any interior foam layers of the off-the-shelf sensor may be discarded, and a new housing (e.g., the housing 138) may be provided. Remanufacturing an off-the-shelf sensor may be desirable in certain embodiments to reduce costs and/or waste.

Figure 9:
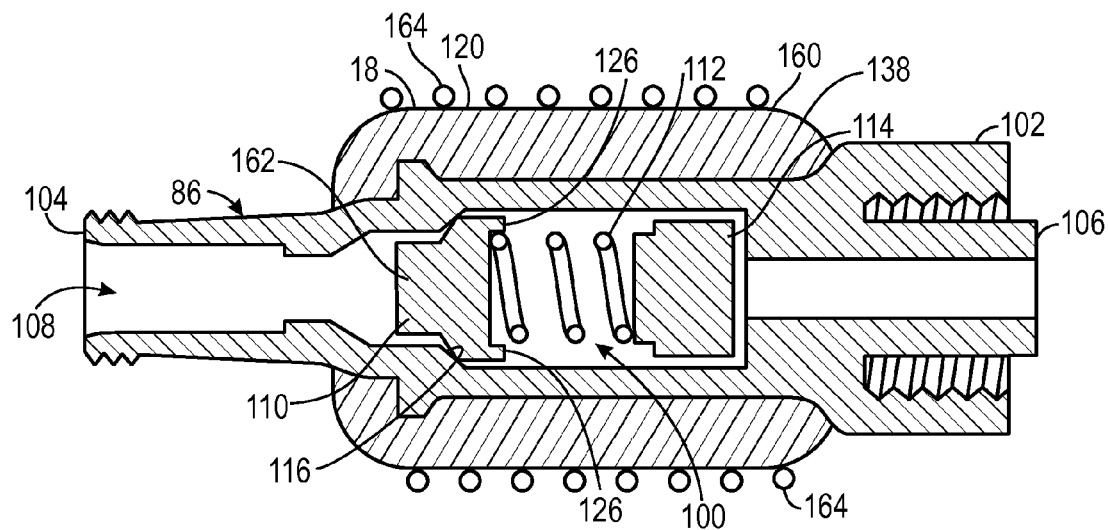
FIG. 9 is cross-sectional view of the connector of FIG. 5 in a closed position and an electromagnetic induction sensor, in accordance with an embodiment.

While the embodiments described above relate to optical detection of the valve stem 110 movement, in other embodiments, movement of the valve stem 110 may be detected using electromagnetic induction. For example, as shown in FIG. 9, the sensor 18 may be an electromagnetic induction sensor 160 configured to detect a current induced by movement of the valve stem 110. For example, the valve stem 110 may be a magnet 162 or may include a magnet (e.g., a magnet embedded within the valve stem 110 and/or a magnetic film disposed about the exterior of the valve stem 110), and the electromagnetic induction sensor 160 may include a coil 164. The coil 164 may be formed from a conductive material, such as coiled aluminum or a coiled copper wire. The movement of the valve stem 110 (e.g., from the closed position to the opened position or vice versa) may cause the magnet 162 to pass through the coil 164, which may generate a current in the coil 164 via electromagnetic induction. The electromagnetic induction sensor 160 may be configured to transmit signals to the monitor 16 relating to the induced current, which may be utilized by the monitor 16 to determine the start and end time of the injection.

The electromagnetic induction sensor 160 may include the housing 138, as described above, to position the electromagnetic induction sensor 160 and the coil 164 about the connector 86 and about the valve assembly 100. In particular, the housing 138 may position the coil 164 about the valve assembly 100 such that the valve stem 110 passes through at least a portion of the coil 164 when the valve stem 110 is displaced during the injection procedure. In certain embodiments, the coil 164 may be integral with (e.g., disposed within) the housing 138. In other embodiments, the coil 164 may be wrapped around the housing 138. In other embodiments, the coil 164 may be a component of the connector 86 instead of the housing 138 of the electromagnetic induction sensor 160. For example, may be wrapped around the magnet 162, wrapped around the housing 102 of the connector 86, or integral with (e.g., disposed within) the housing 102 of the connector 86. In such embodiments, the connector 86 may be communicatively coupled to the monitor 16 via a cable or a wireless communication link and may transmit signals relating to the induced current to the monitor 16. Alternatively, the coil 164 disposed about the magnet 162 or the connector 86 may be electrically coupled to the electromagnetic induction sensor 160 via one or more leads, and the electromagnetic induction sensor 160 may transmit the signals to the monitor 16 for the determination of the start and end time of the injection.

Figure 10:
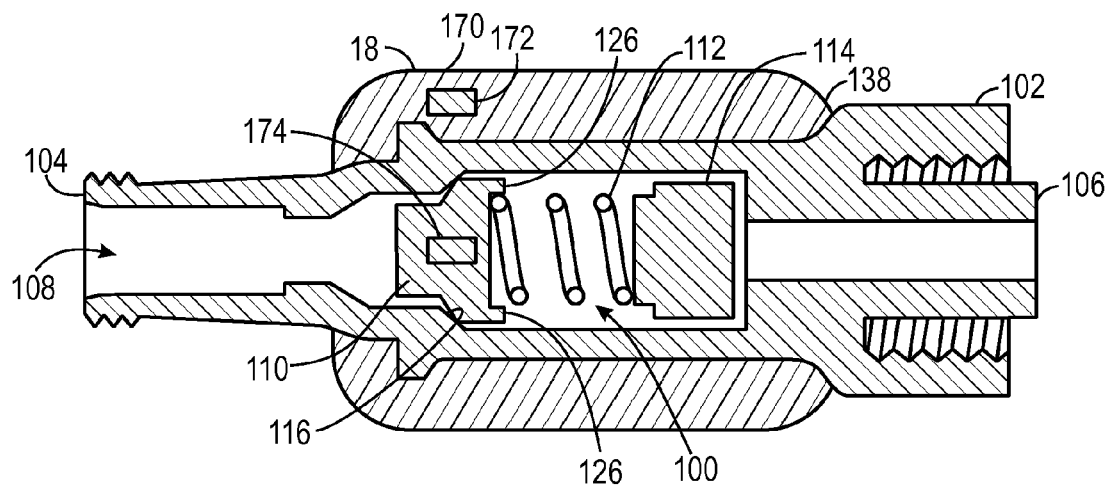
FIG. 10 is cross-sectional view of the connector of FIG. 5 in a closed position and a radio-frequency identification sensor, in accordance with an embodiment.

In other embodiments, movement of the valve stem 110 may be detected using radio-frequency identification (RFID). For example, as shown in FIG. 10, the sensor 18 may be an RFID sensor 170 having an RFID reader 172 configured to detect radio-frequency (RF) signals. In particular, the RFID reader 172 may be configured to read an RFID tag 174 disposed in or on the valve stem 110. The RFID tag 174 may be a passive tag or an active tag. In certain embodiments, the RFID sensor 170 may include the housing 138, as described above, to position the RFID reader 172 about the connector 86. Further, the housing 138 may be configured to position the RFID reader 172 about the connector 86 such that the RFID tag 174 will pass through an interrogation zone of the RFID reader 172 when the RFID tag 174 moves from the closed position to the open position and from the open position to the closed position. As used herein, the interrogation zone is the operating range in which the RFID reader 172 is able to read the RFID tag 174. The interrogation zone of the RFID reader 172 may be selected such that the RFID reader 172 may read the RFID tag 174 when the valve stem 110 is in the open position but not when the valve stem 110 is in the closed position, or vice versa, and may be based at least in part upon the stiffness of the biasing member 112, which may affect the displacement of the valve stem 110. In certain embodiments, the interrogation zone of the RFID reader 172 may be narrow (e.g., approximately 1 centimeter to 3 centimeters in width). Alternatively, the RFID reader 172 may be configured to read the RFID tag 174 when the valve stem 110 is moving between the open and closed positions. In this manner, the RFID reader 172 may be configured to distinguish between the open and closed position. The RFID sensor 170 may transmit signals relating to the position of the valve stem 110 to the monitor, which may be used by the monitor 16 to determine the start and end time of the injection.

Figure 11:
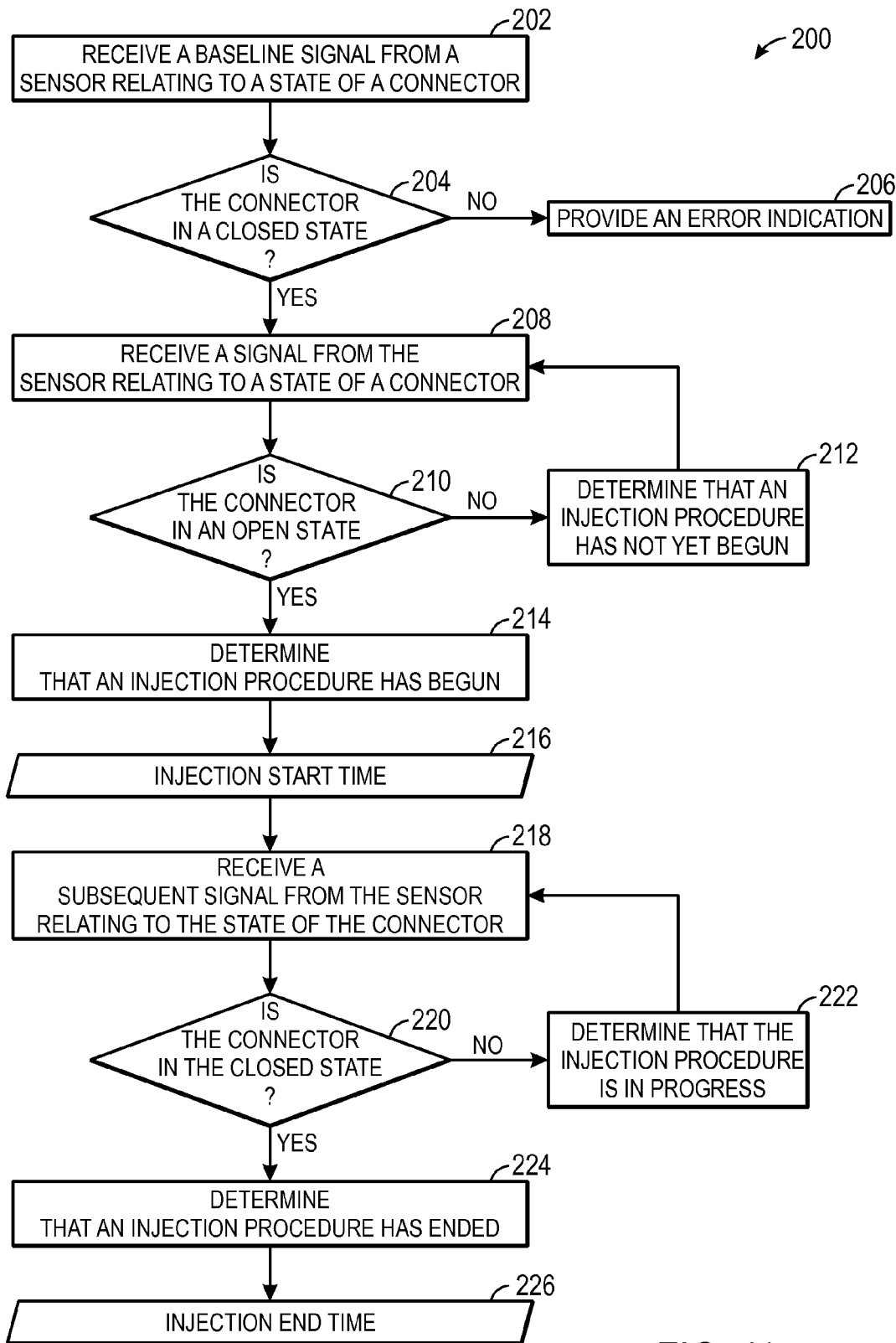
FIG. 11 is a method for determining a start time and an end time of an injection procedure.

As described in detail above, the system 10 as discussed above with respect to FIGS. 1-10 may be configured to determine the start and end time on an injection using signals generated by the one or more sensors 18 (e.g., the optical sensor 120, the electromagnetic induction sensor 150, and/or the RFID sensor 170). Additionally, the present embodiments provide various methods for determining the start and end time of an injection. For example, FIG. 11 illustrates a method 200 for determining a start time and an end time of an injection. The method 200 may be performed as an automated procedure by a system, such as the system 10. In addition, certain steps of the method may be performed by a processor, such as the processor 32, or a processor-based device, such as the monitor 16, that includes instructions for implementing certain steps of the method 200. Further, although the method 200 illustrates steps in a certain sequence, it should be understood that the steps may be performed in any suitable order and certain steps may be carried out simultaneously, where appropriate. Further, certain steps or portions of the methods may be performed by separate devices. In addition, insofar as steps of the methods disclosed herein are applied to the received signals, it should be understood that the received signals may be raw signals or processed signals. That is, the methods may be applied to an output of the received signals.

The method 200 may include receiving a baseline signal from a sensor (e.g., the sensor 18, the optical sensor 120, the electromagnetic induction sensor 150, the RFID sensor 170, or the like) relating to a state of a connector (e.g., the connector 86) (block 202). The baseline signal may be acquired before implementing an injection procedure and may be used to determine whether the connector 86 is operating properly and/or is in the desired initial state, which may be a closed state. The baseline signal may also be advantageous to calibrate the monitor 16 to enable the monitor 16 to more easily detect a change in the signal to determine when the connector 86 is in the open state. The method 200 may also include determining whether the connector 86 is in a closed state based at least in part upon the baseline signal (block 204). As described in detail above, the connector 86 may be in a closed state when the valve stem 110 is in the closed position. If the connector 86 is not in the closed state, the monitor 16 may provide an error indication (block 206). For example, the error indication may be a visible indication, such as a textual message, a graphical indicator, and/or a symbol, on the display 62 of the monitor 16, or an audible indication, such as an alarm, via the speaker 64 of the monitor 16. In certain embodiments, the monitor 16 may additionally provide instructions (e.g., via an indication on the display 62) to correct the error, such as instructions to adjust the valve stem 110 and/or the biasing member 112, to replace the valve assembly 100 of the connector 86, or to replace all of the connector 86, for example.

If the monitor 16 determines that the connector 86 is in the closed position, the method 200 may include receiving a signal from the sensor relating to the state of the connector 86 (block 208). The method 200 may also include determining whether the connector 86 is in an open state based at least in part on the first signal (block 210). As described in detail above, the connector 86 may be in an open state when the valve stem 110 is in the open position. If the monitor 16 determines that the connector 86 is not in the open state, the monitor 16 may determine that the injection procedure has not begun (block 212). That is, the monitor 16 may determine that the injection device 82 is not delivering the indicator to the patient via the connector 86. In certain embodiments, the monitor 16 may be configured to display a visible indication on the display 42 and/or an audible indication via the speaker 44 to provide an indication to the user that the injection procedure has not started. The monitor 16 may continue to receive the signal from the sensor to monitor the state of the connector 86 (block 210).

If the monitor 16 determines that the connector 86 is in the open state, the monitor 16 may determine that the injection procedure has begun (block 214). Based at least in part upon the determination that the injection procedure has begun (block 214), the injection start time may be determined (block 216). The injection start time (block 216) may be saved in the RAM 38 and/or the ROM 56 and may be applied, by the processor 32, to various algorithms for determining physiological parameters of the patient, such as cardiac output. Additionally, the injection start time (block 216) may be displayed on the display 42 of the monitor 16.

The method 200 may also include receiving a subsequent signal (e.g., after the monitor 16 has determined the injection start time (block 216)) from the sensor relating to the state of the connector 86 (block 218). Additionally, the method 200 may include determining whether the connector 86 is in the closed state based at least in part on the subsequent signal (block 220). If the monitor 16 determines that the connector 86 is not in the closed state (i.e., is in the open state), then the monitor 16 may determine that the injection procedure is in progress (block 222). The monitor 16 may continue to receive the subsequent signal from the sensor to monitor the state of the connector 86 (block 218).

If the monitor 16 determines that the connector 86 is in the closed state, the monitor 16 may determine that the injection procedure has ended (block 224). Based at least in part upon the determination that the injection procedure has ended (block 224), the injection end time may be determined (block 226). The injection end time (block 226) may be saved in the RAM 38 and/or the ROM 36 and may be applied, by the processor 32, to various algorithms for determining physiological parameters of the patient, such as cardiac output. Additionally, the injection end time (block 226) may be displayed on the display 42 of the monitor 16. In one embodiment, the injection start time is set to t=0 (i.e. the time of starting the injection is set to zero) based on the data from the sensor 18, and the blood flow rate at the outlet point for the photoacoustic measurement is:

$$F = \frac{V_{It}}{\int_0^\infty \frac{V_I(t)}{V} dt} \quad (1)$$

where V and VI(t) are blood volume and isotonic volume rates during the unit time interval, Δt, respectively, in the sectional surface at the outlet point. The unit time interval, Δt, represents the time interval for data acquired from a photoacoustic sensor 20.

While the above embodiments relate to determining the start and end time of an injection based on determined positions of the valve stem 110, the system 10 may additionally or alternatively utilize signals generated from sensors 18 that may be configured to acquire pressure, temperature, and/or flow rate measurements from components of the system 10 that may be indicative of the start and/or end of an injection. In particular, the sensors 18 may be configure to acquire measurements from components of the injection assembly 12 (e.g., tubing of the injection assembly 12, the injection device 82, the connector 86, the catheter 80, and/or the patient 14).

Figure 12:
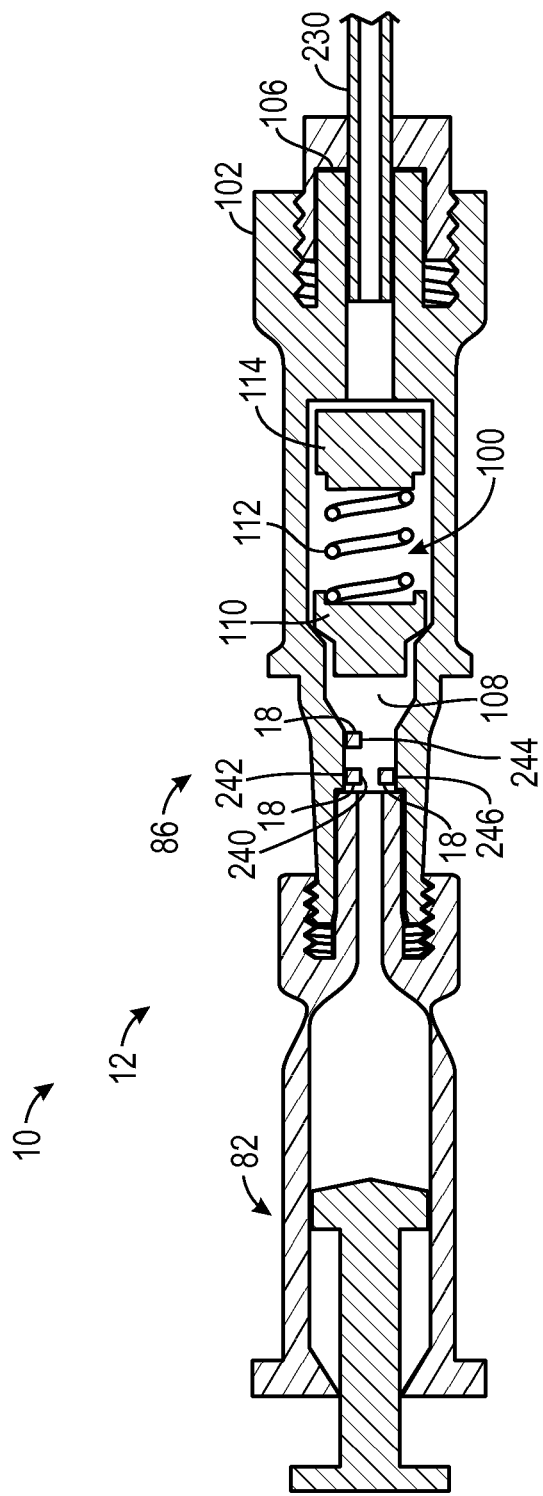
FIG. 12 is a cross-sectional view of the connector of FIG. 5 and sensors disposed in the connector.

For example, as shown in FIG. 12, which illustrates the injection device 82, tubing 230, which may couple to the catheter 80, and the embodiment of the connector 86 described in FIGS. 4-10, the system 10 may include sensors 18 downstream from the injection device 82 to detect changes in pressure, temperature, and/or flow rate resulting from the injection of the indicator. As illustrated, the sensors 18 may be disposed in the passageway 108 of the connector 86 close to (e.g., proximate) a tip 240 of the injection device 82. In certain embodiments, the sensors 18 may be disposed between approximately 1 millimeter to 50 millimeters, 2 millimeters to 30 millimeters, 3 millimeters to 20 millimeters, or 4 millimeters to 10 millimeters from the tip 240 of the injection device 82. This may be desirable in certain embodiments to reduce delay in detecting the start of an injection. However, as noted above, the sensors 18 may be positioned in any suitable location. For example, in other embodiments, the sensors 18 may be positioned side-stream to the lumen 108.

In certain embodiments, at least one of the one or more sensors 18 may include a pressure sensor 242 configured to acquire pressure measurements. The pressure sensor 242 may transmit pressure signals to the monitor 16, and the monitor 16 may utilize the pressure signals to determine the start and end of an injection procedure. In particular, the pressure in the passageway 108 may increase in response to the injected indicator, which may indicate the start of an injection, and may decrease after the injection procedure is finished, which may indicate the end of an injection. In certain embodiments, the monitor 16 may compare the pressure detected by the pressure sensor 242 to a predetermined pressure threshold and/or a change in pressure to a predetermined change in pressure threshold, which may each be stored in the RAM 38 and/or the ROM 36, to determine whether the indicator is flowing through the passageway 108.

Additionally or alternatively, at least one of the one or more sensors 18 may include a temperature sensor 244 configured to acquire temperature measurements. The temperature sensor 244 may transmit temperature signals to the monitor 16, and the monitor 16 may utilize the temperature signals to determine the start and end of an injection procedure. In particular, the temperature in the passageway 108 may increase or decrease in response to the injected indicator depending on the temperature of the injected indicator, which may indicate the start of an injection, and may return to a baseline temperature after the injection procedure is finished, which may indicate the end of an injection. In certain embodiments, the monitor 16 may compare the temperature detected by the temperature sensor 244 to a temperature predetermined threshold and/or a change in temperature to a predetermined change in temperature threshold, which may each be stored in the RAM 38 and/or the ROM 36, to determine whether the indicator is flowing through the passageway 108. It should be noted that the predetermined temperature threshold may be dependent upon the temperature of the injected indicator. Accordingly, multiple predetermined temperature thresholds may be stored in the RAM 38 and/or the ROM 36 for various indicator temperatures, and the monitor 16 may be configured to select the appropriate predetermined temperature threshold based on the indicator temperature, which may be inputted by a user via the user inputs 40.

Further, at least one of the one or more sensors 18 may include a flow rate sensor 246 configured to acquire flow rate measurements (e.g., the speed of the indicator as it travels through the passageway 108). In particular, the flow rate sensor 246 may include an orifice (not shown) to enable the indicator to flow through the flow rate sensor 246, and the flow rate sensor 246 may be configured to measure the pressure upstream and downstream from the orifice of the flow rate sensor 246 and may calculate the flow rate using the known diameter of the orifice. The flow rate sensor 246 may transmit flow rate signals to the monitor 16, and the monitor 16 may utilize the flow rate signals to determine the start and end of an injection procedure. In particular, the flow rate in the passageway 108 may increase in response to the injected indicator, which may indicate the start of an injection, and may decrease after the injection procedure is finished, which may indicate the end of an injection. In certain embodiments, the monitor 16 may compare the flow rate detected by the flow rate sensor 246 to a predetermined flow rate threshold and/or a change in flow rate to a predetermined change in flow rate threshold, which may each be stored in the RAM 38 and/or the ROM 36, to determine whether the indicator is flowing through the passageway 108.

Further, in addition to determining the start and end time of the injection procedure, the monitor 16 may also be configured to determine quality information relating to the injection procedure. This may be particularly desirable in embodiments in which the injection device 26 is a manual device. That is, a user may experience difficulty in injecting the indicator at a constant rate, and fluctuations in the injection profile may adversely affect the accuracy of the indicator dilution procedure. Accordingly, in some embodiments, the monitor 16 may be configured to periodically or continuously monitor measurements from the one or more sensors 18 (e.g., the pressure sensor 242, the temperature sensor 244, and/or the flow rate sensor 246) and may determine information relating to the injection profile based on the signals from the one or more sensors 18. For example, the monitor 16 may be configured to determine information such as variations in the speed, pressure, and/or temperature of the injection. In certain embodiments, the monitor 16 may determine the standard deviation (e.g., the spread or the variability), the mean, or any other suitable parameter of the speed, pressure and/or temperature of the injection and may compare the determined parameter to a respective threshold or threshold range. If the determined parameter is outside of its respective threshold or threshold range, the monitor 16 may determine and/or alert a user that the injection profile may adversely affect the accuracy of the indicator dilution procedure and that it may be desirable for the user to perform the injection procedure again. For example, the monitor 16 may be configured to display an indication via the display 42 and/or the speaker 44 that it may be desirable for the user to perform the injection procedure again.

The disclosed embodiments are provided in the context of an indicator dilution system. However, it should be understood that the features described herein may be incorporated into any system configured to deliver a predetermined volume of a fluid to a patient. Furthermore, the various features and techniques described herein may be combined or utilized together in any suitable manner to determine whether an injection device, automated or manual, is delivering a fluid (e.g., an indicator) to a patient and to determine the start and the end time of the injection. While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A sensor assembly comprising:
   a connector comprising:
      a first end configured to be coupled to an injection device configured to inject a fluid;
      a second end configured to be coupled to tubing configured to deliver the fluid to a patient such that the connector, when coupled, is between the tubing and the injection device;
      a lumen extending from the first end to the second end;
      a valve assembly configured to enable flow of the fluid through the lumen when the connector is in an open state and to reduce flow of the fluid through the lumen when the connector is in a closed state; and
      an optical sensor configured to generate a signal relating to whether the connector is in the open state or the closed state, wherein the optical sensor comprises a sensor housing, an emitter, and a detector, and the sensor housing is removably attachable to an exterior surface of the connector, and wherein the sensor housing comprises a flexible substrate configured to at least partially wrap around the connector and an adhesive layer to removably attach the sensor housing to the exterior surface of the connector.

2. The sensor assembly of claim 1, wherein the valve assembly comprises:
   a valve stem configured to move relative to a housing of the connector into an open position and an closed position, wherein connector is in the closed state when the valve stem is in the closed position and is in the open state when the valve stem is in the open position; and
   a biasing member coupled to the valve stem and configured to bias the valve stem in the closed position, wherein the valve stem is configured to move to the open position when the injection device delivers the fluid to the connector at a pressure above a predetermined threshold.

3. The sensor assembly of claim 2, wherein the connector is a pressure-activated luer check valve.

4. The sensor assembly of claim 2, wherein the optical sensor is configured to generate a signal relating to the position of the valve stem.

5. The sensor assembly of claim 4, wherein an optical path of the optical sensor is substantially perpendicular to movement of the valve stem.

6. The sensor assembly of claim 4, wherein the valve stem is opaque, and wherein the housing of the connector is at least partially transparent.

7. The sensor assembly of claim 5, wherein the sensor housing is configured to position the emitter and the detector about the connector such that the valve stem blocks at least a portion of the optical path of the optical sensor when the valve stem is in the closed position and does not block the optical path when the valve stem is in the open position.

8. The sensor assembly of claim 5, wherein the sensor housing is configured to position the emitter and the detector about the connector such that the valve stem blocks at least a portion of the optical path of the optical sensor when the valve stem is in the open position and does not block the optical path when the valve stem is in the closed position.

9. The sensor assembly of claim 1, wherein the sensor housing comprises an alignment feature configured to mate with a complementary alignment feature of the connector.

10. The sensor assembly of claim 1, wherein the sensor assembly is removably coupled to the tubing and the injection device.

11. The sensor assembly of claim 1, wherein the first end is removably attachable to a complementary mating connector of the injection device.

12. The sensor assembly of claim 1, wherein the sensor comprises a memory storing a first light intensity threshold indicative of a blocked optical path, a second light intensity threshold indicative of an unblocked optical path, or both.

13. The sensor assembly of claim 1, wherein the optical sensor comprises a pulse oximetry sensor.

14. A sensor assembly, comprising:
    a connector comprising:
       a first end removably attachable to an injection device;
       a second end removably attachable to tubing configured to deliver a fluid from the injection device to a patient such that the connector, when attached, is between the tubing and the injection device;
       a lumen extending from the first end to the second end; and
       a valve assembly extending into the lumen to enable flow of the fluid through the lumen when the connector is in an open state and to reduce flow of the fluid through the lumen when the connector is in a closed state; and
    a bandage-type sensor coupled to an exterior surface of the connector and positioned to detect whether the connector is in the open state or the closed state.

15. The sensor assembly of claim 14, wherein the bandage-type sensor comprises an adhesive layer configured to removably attach the bandage-type sensor to the exterior surface of the connector.

16. The sensor assembly of claim 14, wherein the valve assembly comprises:
    a valve stem movable relative to a housing of the connector into an open position and an closed position, wherein the connector is in the closed state when the valve stem is in the closed position and is in the open state when the valve stem is in the open position; and
    a biasing member coupled to the valve stem and biasing the valve stem toward the closed position, wherein the valve stem is movable into the open position when the injection device delivers the fluid to the connector at a pressure above a predetermined threshold;
    wherein the bandage-type sensor is configured to generate a signal relating to a position of the valve stem.

17. The sensor assembly of claim 16, wherein the connector is a pressure-activated luer check valve.

18. The sensor assembly of claim 16, wherein the bandage-type sensor is configured to generate a signal relating to the position of the valve stem.

19. The sensor assembly of claim 18, wherein the valve stem is opaque, and wherein the housing of the connector is at least partially transparent.

20. The sensor assembly of claim 18, wherein the bandage-type sensor comprises an emitter and a detector, and wherein an optical path of the bandage-type sensor is substantially perpendicular to movement of the valve stem.

21. The sensor assembly of claim 20, wherein a sensor housing of the bandage-type sensor is configured to position the emitter and the detector about the connector such that the valve stem blocks at least a portion of the optical path of the bandage-type sensor when the valve stem is in the closed position and does not block the optical path when the valve stem is in the open position.

22. The sensor assembly of claim 20, wherein a sensor housing of the bandage-type sensor is configured to position the emitter and the detector about the connector such that the valve stem blocks at least a portion of the optical path of the bandage-type sensor when the valve stem is in the open position and does not block the optical path when the valve stem is in the closed position.

23. The sensor assembly of claim 20, wherein the bandage-type sensor comprises a memory storing a first light intensity threshold indicative of a blocked optical path, a second light intensity threshold indicative of an unblocked optical path, or both.

24. A sensor assembly, comprising:
  a connector comprising:
    a first end configured to be coupled to an injection device configured to inject a fluid;
    a second end configured to be coupled to tubing configured to deliver the fluid to a patient such that the connector, when coupled, is between the tubing and the injection device;
    a lumen extending from the first end to the second end; and
    a valve assembly configured to enable flow of the fluid through the lumen when the connector is in an open state and to reduce flow of the fluid through the lumen when the connector is in a closed state; and
  an optical sensor configured to generate a signal relating to whether the connector is in the open state or the closed state, wherein the optical sensor comprises a sensor housing, an emitter, and a detector, and the sensor housing is removably attachable to an exterior surface of the connector, and wherein the optical sensor comprises a bandage-type pulse oximetry sensor, and wherein the bandage-type pulse oximetry sensor is configured to be wrapped around the exterior surface of the connector.

25. The sensor assembly of claim 24, wherein the valve assembly comprises:
  a valve stem configured to move relative to a housing of the connector into an open position and an closed position, wherein connector is in the closed state when the valve stem is in the closed position and is in the open state when the valve stem is in the open position; and
  a biasing member coupled to the valve stem and configured to bias the valve stem in the closed position, wherein the valve stem is configured to move to the open position when the injection device delivers the fluid to the connector at a pressure above a predetermined threshold.

26. The sensor assembly of claim 25, wherein the connector is a pressure-activated luer check valve.

27. The sensor assembly of claim 25, wherein the bandage-type pulse oximetry sensor is configured to generate a signal relating to the position of the valve stem.

28. The sensor assembly of claim 27, wherein the valve stem is opaque, and wherein the housing of the connector is at least partially transparent.

29. The sensor assembly of claim 27, wherein an optical path of the bandage-type pulse oximetry sensor is substantially perpendicular to movement of the valve stem.

30. The sensor assembly of claim 29, wherein the sensor housing is configured to position the emitter and the detector about the connector such that the valve stem blocks at least a portion of the optical path of the bandage-type pulse oximetry sensor when the valve stem is in the closed position and does not block the optical path when the valve stem is in the open position.

31. The sensor assembly of claim 29, wherein the sensor housing is configured to position the emitter and the detector about the connector such that the valve stem blocks at least a portion of the optical path of the bandage-type pulse oximetry sensor when the valve stem is in the open position and does not block the optical path when the valve stem is in the closed position.

32. The sensor assembly of claim 24, wherein the sensor housing comprises an alignment feature configured to mate with a complementary alignment feature of the connector.

33. The sensor assembly of claim 24, wherein the sensor assembly is removably coupled to the tubing and the injection device.

34. The sensor assembly of claim 24, wherein the first end is removably attachable to a complementary mating connector of the injection device.

35. The sensor assembly of claim 24, wherein the bandage-type pulse oximetry sensor comprises a memory storing a first light intensity threshold indicative of a blocked optical path, a second light intensity threshold indicative of an unblocked optical path, or both.

\* \* \* \* \*